(12) United States Patent
Hercek et al.

(10) Patent No.: US 7,534,895 B2
(45) Date of Patent: May 19, 2009

(54) PROCESS FOR PREPARATION OF CARVEDILOL

(75) Inventors: Richard Hercek, Hlohovec (SK); Alojz Skoda, Hlohovec (SK); Bohumil Proksa, Hlohovec (SK)

(73) Assignee: Zentiva, A.S., Hlohovec (SK)

( * ) Notice: Subject to any disclaimer, the term of this patent is extended or adjusted under 35 U.S.C. 154(b) by 600 days.

(21) Appl. No.: 10/533,809

(22) PCT Filed: Nov. 4, 2003

(86) PCT No.: PCT/SK03/00020

§ 371 (c)(1),
(2), (4) Date: May 5, 2005

(87) PCT Pub. No.: WO2004/041783

PCT Pub. Date: May 21, 2004

(65) Prior Publication Data

US 2006/0167077 A1    Jul. 27, 2006

(30) Foreign Application Priority Data

Nov. 8, 2002  (SK) ................... 1595-2002

(51) Int. Cl.
*C07D 209/82*   (2006.01)

(52) U.S. Cl. .................................. 548/444
(58) Field of Classification Search .................. 548/444
See application file for complete search history.

(56) References Cited

U.S. PATENT DOCUMENTS 4,503,067 A    3/1985   Wiedemann et al.

FOREIGN PATENT DOCUMENTS

| EP | 0 127 099 | 12/1984 |
|----|-----------|---------|
| EP | 0 918 055 | 5/1999  |
| WO | 02/00216  | 1/2002  |

*Primary Examiner*—James O. Wilson
*Assistant Examiner*—Ebenezer Sackey
(74) *Attorney, Agent, or Firm*—Oblon, Spivak, McClelland, Maier & Neustadt, P.C.

(57) ABSTRACT

The invention solves a new method of preparation of Carvedilol for pharmaceutical use. In the synthesis of Carvedilol a reaction of 4-(oxirane-2-ylmethoxy)-9H-arbazole (II) with 2-(2-methoxyphenoxy)ethylamine salts (IV) in the presence of a base, in an alcohol having the number of carbons C2 to C5 as a solvent, at an elevated temperature, is used. After processing of the crude reaction mixture crude Carvedilol is obtained, which is purified by crystallization from ethylacetate with an addition of activated carbon and the final substance is formulated by crystallization from ethylacetate.

16 Claims, No Drawings

PROCESS FOR PREPARATION OF CARVEDILOL

TECHNICAL FIELD

This invention belongs to the field of the pharmaceutical production and relates to synthesis and purification of the active substance Carvedilol.

BACKGROUND ART

Carvedilol, (±) 1-(9H-carbazol-4-yloxy)-3-[[2-(2-methoxyphenoxy)-ethyl]-amino]-2-propanol of structure I, is a combined alpha- and betalytic with vasodilating activity.

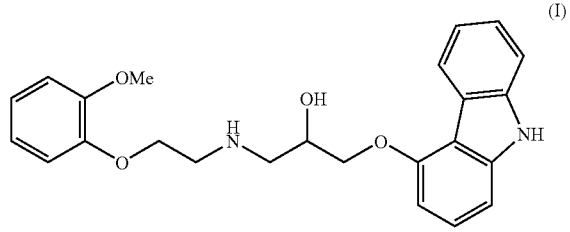

According to DE 2815926 (U.S. Pat. No. 4,503,067) Carvedilol is prepared by the reaction of 4-(oxirane-2-ylmethoxy)-9H-carbazole (II) with 2-(2-methoxyphenoxy) ethylamine (III).

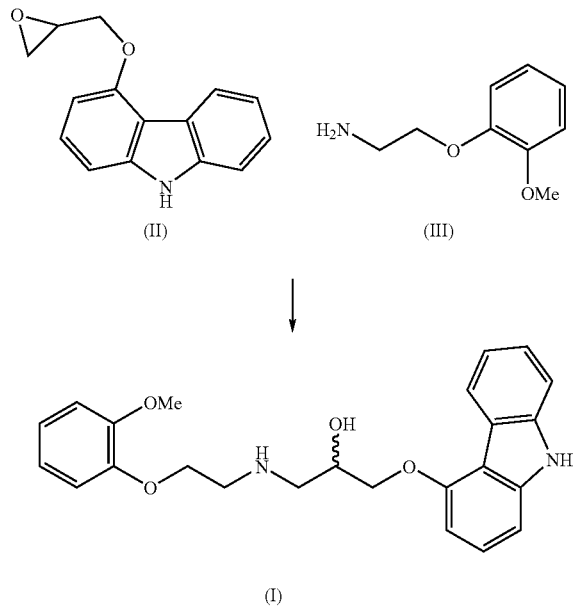

By the method described, Carvedilol is prepared in low yields, moreover contaminated with the bis-derivative. This problem is solved by the method according to EP 918 055, in which 4-(oxirane-2-ylmethoxy)-9H-carbazole (II) is coupled with N-benzylated 2-(2-methoxyphenoxy)ethylamine; by this method creation of bis-derivative is minimized and the yield of Carvedilol is increased, but a disadvantage of this method is introducing of an additional step—hydrogenolytic removal of the protective benzyl group on a palladium catalyst.

Another method of decreasing the amount of the bis-derivative and thus increasing the yield of the product in the process of preparation of Carvedilol is described in WO 0200216, wherein an epoxide (II) reacts with an amine (III) in a solvent or without any solvent, the product being isolated after the reaction in the form of Carvedilol hydrochloride hydrate from the reaction mixture after adding water, ethylacetate and diluted hydrochloric acid.

All the abovementioned methods of preparation of Carvedilol use, as one of the starting materials, the amine base (III), or its N-benzylated derivative, which have low stability—they are subject to decomposition in contact with air and light. The abovementioned disadvantages are solved by the method of this invention.

DISCLOSURE OF INVENTION

In the preparation of Carvedilol according to this invention 4-(oxirane-2-ylmethoxy)-9H-carbazole (II) reacts with salts of 2-(2-methoxyphenoxy)ethylamine (III), which can contain 0 to 10% water, in the presence of a base in an organic solvent. From the abovementioned salts of 2-(2-methoxyphenoxy) ethylamine, for example, hydrogenchloride, hydrogenbromide, hydrogentartrate, hydrogenoxalate or hydrogensulphate can be used, preferably 2-(2-methoxyphenoxy) ethylamine hydrogenchloride monohydrate (IV) in an amount of 2 to 5 equivalents, based on the starting carbazole (II). The reaction is carried out in the presence of 2 to 5 equivalents of a base, which is an alkali metal or alkaline earth metal carbonate, in an organic solvent, which is an alcohol having the number of carbons C2 to C5, preferably in the presence of anhydrous potassium carbonate in isopropanol. After the reaction is finished, the solids are removed from the reaction mixture by filtration or centrifugation between the temperatures of 20 to 50° C., the liquid portion is concentrated to ¹/₁₀ of the initial volume, the residue is diluted under heating in ethylacetate in the ratio 1:1 to 1:5, cooled to a temperature between 25 to 40° C. and after precipitating the crystal, the mixture is cooled to a temperature between 0 to 10° C., the precipitated Carvedilol being isolated by filtration or centrifugation and further purified by crystallisation.

In comparison with other known methods, the method of production of Carvedilol of this invention is more advantageous in that a salt of 2-(2-methoxyphenoxy)ethylamine is used, which is, in comparison with the base, more stable and more available and it does not bring higher technical and economic requirements for the industrial realisation of the production of Carvedilol.

A surprising and new fact in the inventive method of production is that the method is advantageous in obtaining crude Carvedilol having up to three times lower contents of the bis-derivative than using existing known methods.

The method of preparation of Carvedilol of this invention is also advantageous in that the new conditions of the preparation in combination with purification and isolation of the substance increase the yield of the product and its purity and guarantee reliability of the production of an acceptable substance in required pharmacopoeial quality and with a defined particle size.

Methods of production of this invention will be clear from the following examples, which, however, do not limit the same in any case.

EXAMPLES

Example 1

To a mixture of 5.0 kg anhydrous potassium carbonate and 7.5 kg of 2-(2-methoxyphenoxy)ethylamine hydrogenchloride monohydrate (IV) in 32 liters of isopropanol, mixed at a temperature of 35° C. for 15 min., are added 3.87 kg of 4-(oxirane-2-ylmethoxy)-9H-carbazole (II) and the mixture is, with intensive stirring, heated at 83° C. for 5 hours. After the epoxide has reacted, the reaction mixture is filtered, isopropanol is distilled off and the residue is diluted in 20 l ethylacetate. The obtained solution is cooled, inoculated and stirred at the temperature of 35° C. for 30 minutes. After the crystal precipitates, the mixture is cooled to 5° C. and stirred for four hours. The crystallised raw Carvedilol is centrifuged and washed with cooled ethylacetate (HPLC contents>98 area %, HPLC contents of the bis-derivative 1.2-1.5 area %).

The moist, crude Carvedilol is diluted at a temperature of 55 to 65° C. in 30 l ethylacetate, 0.8 kg of activated carbon is added, and stirred for 30 minutes at a temperature of 65 to 72° C. Then the mixture is filtered, cooled to a temperature of 45 to 55° C. and it is stirred. After the crystal precipitates, the mixture is cooled to a temperature of 0 to 10° C. and is further stirred for four hours. The crystallised, purified Carvedilol is centrifuged, washed with cooled ethylacetate and dried at the temperature of 40° C.

The purified Carvedilol is recrystallised by the same method from 23 liters of ethylacetate. After drying at the temperature of 40° C. the Carvedilol substance is obtained in 45% yield, of pharmacopoeial quality and of defined particle size.

Example 2

A mixture of 9.7 g 4-(oxirane-2-ylmethoxy)-9H-carbazole (II), 53.7 g of anhydrous hydrogen sulphate of 2-(2-methoxyphenoxy)ethylamine (III) and 28 g of anhydrous potassium carbonate in 200 ml isopropanol are, with intensive stirring, heated at 80° C. for six hours. When the epoxide has reacted, the mixed salts are filtered off from the reaction mixture and isopropanol is distilled off from the filtrate. The obtained honey-like concentrate is diluted with heating in 50 ml of ethylacetate, the solution is cooled to the temperature of 40° C., it is inoculated and stirred at the temperature of 40° C. for two hours. After the crystal precipitates, the mixture is cooled to the temperature of 0° C., and is kept like that with stirring for a minimum of four hours. After filtration and washing with cooled ethylacetate, 5.2 g of wet, crude Carvedilol is obtained (HPLC contents 95.2 area %, HPLC contents of the bis-derivative 2.8 area %).

Example 3

A mixture of 43.2 g 4-(oxirane-2-ylmethoxy)-9H-carbazole (II), 80.0 g of 2-(2-methoxyphenoxy)ethylamine hydrogenchloride monohydrate (IV) and 52.4 g of anhydrous calcium carbonate in 330 ml isopropanol is, with intensive stirring, heated at 80° C. for 4 hours. When the epoxide has reacted, the mixed salts are filtered off from the reaction mixture and isopropanol is distilled off from the filtrate. The obtained honey-like concentrate is dissolved, when hot, in 210 ml of ethylacetate, the solution is cooled to the temperature of 40° C., inoculated and stirred at the temperature of 40° C. for 30 minutes. After the crystal precipitates, the mixture is cooled to 0° C., and is kept like that with stirring for a minimum of four hours. After filtration and washing with cooled ethylacetate, 65 to 70 g of wet crude Carvedilol is obtained (HPLC contents>98 area %, HPLC contents of the bis-derivative 1.2-1.5 area %).

Example 4

To a mixture of 245.2 g of anhydrous potassium carbonate and 374.5 g of 2-(2-methoxyphenoxy)ethylamine hydrogenchloride monohydrate (IV) in 1000 ml of isoamyl alcohol, stirred at the temperature of 80° C., are added, in four portions during 5 hours, a total of 202.1 g of 4-(oxirane-2-ylmethoxy)-9H-carbazole (II). After adding the whole amount the reaction mixture is stirred for two further hours at a temperature of 80 to 85° C. When the epoxide has reacted the mixed salts are filtered off from the reaction mixture and isoamyl alcohol is distilled off from the filtrate. A honey-like concentrate is, when hot, dissolved in 1000 ml of ethylacetate, the solution is cooled to the temperature of 30° C., inoculated, and stirred for 30 minutes. After the crystal precipitates, the mixture is cooled to 0° C. and stirred for 5 hours. The crystallised crude Carvedilol is filtered off and washed with cooled ethylacetate.

The wet crude Carvedilol is dissolved while hot in 1000 ml of ethylacetate, activated carbon is added and the mixture is stirred for a further 30 minutes. Then the mixture is filtered through diatomaceous earth and the filter is washed with 500 ml of hot ethylacetate. The filtrate is cooled to the temperature of 45° C. and stirred for 30 minutes, then it is cooled down to the temperature of 5° C. and stirred for 4 hours. The crystallised, purified Carvedilol is filtered off, washed with cooled ethylacetate and dried.

The obtained, purified Carvedilol is recrystallised from 1000 ml ethylacetate, the crystallised Carvedilol substance is centrifuged, washed with cooled ethylacetate and dried at the temperature of 40° C. in a vacuum drier, product being obtained in 41% yield.

INDUSTRIAL APPLICABILITY

This invention can be used in the pharmaceutical industry for the production of Carvedilol, which is used in medical practice as a combined alpha- and betalytic with vasodilating activity.

The invention claimed is:

1. A method of preparation of Carvedilol, comprising the reaction of 4-(oxirane-2-ylmethoxy)-9H-carbazole with 2.0 to 5.0 equivalents of a salt of 2-(2-methoxyphenoxy)-ethylamine with respect to the carbazole, wherein said salt can contain 0 to 10% water, in the presence of a base which is an alkali metal or alkaline earth metal carbonate present in an amount of 2.0 to 5.0 equivalents with respect to the starting carbazole, in a solvent selected from the group consisting of C2 to C5 alcohols, and wherein after completion of the reaction Carvedilol is present in the reaction mixture.

2. The method of claim 1, wherein the solvent is isopropanol.

3. The method of claim 1, wherein the base is potassium carbonate or calcium carbonate.

4. The method of claim 1, wherein the reaction temperature is maintained in the range of 75 to 85° C.

5. The method of claim 1, further comprising, after completion of the reaction, the reaction mixture is depleted of solids, the liquid portion is concentrated, the residue is dissolved in an organic solvent, cooled down and crystallized to give crude Carvedilol, which is separated and re-crystallized.

6. The method of claim 5, wherein the solids are separated by filtration or centrifuging within the temperature range of 20 to 50° C.

7. The method of claim 5, wherein the liquid portion is concentrated to 1/10 of the initial volume, the concentrate is dissolved in ethylacetate in a ratio 1:1 to 1:5, cooled down to a temperature 25 to 40° C. and after the crystal falls out the mixture is cooled down to a temperature 0 to 10° C., Carvedilol being isolated by filtration or centrifuging.

8. The method of claim 1, wherein the solvent is isoamyl alcohol.

9. The method of claim 1, wherein the carbonate is anhydrous potassium carbonate or anhydrous calcium carbonate.

10. The method of claim 1, wherein the salt of 2-(2-methoxyphenoxy)-ethylamine is a hydrogen chloride monohydrate salt, the base is anhydrous potassium carbonate, and the solvent is isopropanol.

11. The method of claim 1, wherein the salt of 2-(2-methoxyphenoxy)-ethylamine is a hydrogen sulphate salt, the base is anhydrous potassium carbonate, and the solvent is isopropanol.

12. The method of claim 1, wherein the salt of 2-(2-methoxyphenoxy)-ethylamine is a hydrogen chloride monohydrate salt, the base is anhydrous calcium carbonate, and the solvent is isopropanol.

13. The method of claim 1, wherein the salt is the hydrogen chloride monohydrate salt, the base is anhydrous potassium carbonate, and the solvent is isoamyl alcohol.

14. The method of claim 1, wherein the salt of 2-(2-methoxyphenoxy)-ethylamine in the solvent in the presence of the carbonate base in the reaction mixture is more stable to decomposition than the stability of 2-(2-methoxyphenoxy)-ethylamine in the solvent.

15. The method of claim 1, wherein the yield of Carvediol ranges from 41 to 45%.

16. The method of claim 1, whereby Carvedilol is obtained having a bis-derivative content, as determined by HPLC, of 1.2 to 2.8 area %.

* * * * *